United States Patent
Sato et al.

(10) Patent No.: US 6,169,108 B1
(45) Date of Patent: Jan. 2, 2001

(54) ANHYDROUS CRYSTALS

(75) Inventors: Yukio Sato; Hiroaki Kitaoka; Tatsuya Terada; Makoto Ono, all of Tokyo (JP)

(73) Assignee: Daiichi Pharmaceutical Co., Ltd., Tokyo (JP)

(*) Notice: Under 35 U.S.C. 154(b), the term of this patent shall be extended for 0 days.

(21) Appl. No.: 08/913,615

(22) PCT Filed: Mar. 1, 1996

(86) PCT No.: PCT/JP96/00485

§ 371 Date: Nov. 7, 1997

§ 102(e) Date: Nov. 7, 1997

(87) PCT Pub. No.: WO96/29308

PCT Pub. Date: Sep. 26, 1996

(30) Foreign Application Priority Data

Mar. 23, 1995 (JP) .................................... 7-064234
Apr. 20, 1995 (JP) .................................... 7-094782

(51) Int. Cl.$^7$ .......................... A61K 31/40; C07D 207/27
(52) U.S. Cl. ........................ 514/423; 548/541; 548/550
(58) Field of Search ..................... 548/550, 541; 514/423

(56) References Cited

U.S. PATENT DOCUMENTS 4,341,790 * 7/1982 Betzing et al. .................... 424/274
5,461,157 * 10/1995 Kamihara et al. .................. 548/550

FOREIGN PATENT DOCUMENTS 574952    12/1993  (EP).
6-65197    3/1994  (JP).

* cited by examiner

Primary Examiner—Cecilia Tsang
Assistant Examiner—Ebenezer Sackey
(74) Attorney, Agent, or Firm—Greenblum & Bernstein, P.L.C.

(57) ABSTRACT

An anhydrous crystal of a compound represented by the formula: $R^2$—$CH_2CONH$—$R^1$ wherein $R^1$ represents a substituted or non-substituted pyridyl group or substituted or non-substituted phenyl group and $R^2$ represents a substituted or non-substituted 2-oxo-1-pyrrolidinyl group, characterized in that said crystal is substantially free from hygroscopicity. For example, by drying a hydrous crystal of said compound at a temperature of 80° C. or above under reduced pressure, an anhydrous crystal is provided that exhibits a weight increase of 1% or less when stored under the relative humidity of 83% at the temperature of 25° C. for 30 days. By using the anhydrous crystal for the manufacture of a medicament comprising the compound as an active ingredient, a product with a constant content of the active ingredient can be obtained.

17 Claims, 1 Drawing Sheet

ANHYDROUS CRYSTALS

TECHNICAL FIELD

This apply is a 371 at PCT/JP96/00485 filed Mar. 1, 1996.

The present invention relates to a method for preparing pyrrolidinylacetamide derivatives as anhydrous crystals which are suitable as pharmaceutical bulk powders. More specifically, the present invention relates to a method for preparing anhydrous crystals of pyrrolidinylacetamide derivatives which are substantially free from hygroscopicity when stored under a highly humid condition for a long period of time.

BACKGROUND ART

The compound represented by the following formula:

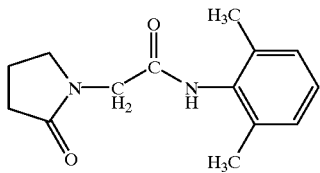

[N-(2,6-dimethylphenyl)-2-(2-oxo-1-pyrrolidinyl) acetamide; referred to as Compound (1) hereinafter in the specification] has been expected to be a cognition-enhancing agent (see, the Japanese Patent Unexamined Publication (KOKAI) No. (Hei) 6-65197/1994). An anhydrous crystal of Compound (1) can be prepared from a hydrous crystal of said compound.

In the course of preparations of the anhydrous crystals of the aforementioned compound, the inventors of the present invention have encountered significant differences in hygroscopicity among the lots of anhydrous crystals, and found that the differences were due to the existence of several sorts of anhydrous crystals having distinguishable hygroscopic rates. In addition, they first found that a main cause of resulting the crystals with different hygroscopic rates was attributable to drying conditions for preparing anhydrous crystals by drying the hydrate.

In order to maintain constant quality of pharmaceutical preparations, it is desired to use anhydrous crystals substantially free from hygroscopicity as bulk powders. However, substantially non-hygroscopic anhydrous crystals of the aforementioned compound have not yet been known to date.

DISCLOSURE OF THE INVENTION

An object of the present invention is to provide an anhydrous crystal of the aforementioned compound that is substantially free from hygroscopicity. Another object of the present invention is to provide a novel method for preparation that can produce the anhydrous crystal in a large scale with excellent reproducibility.

The inventors of the present invention conducted various researches to achieve the foregoing objects, and as a result, they found that an anhydrous crystal substantially free from hygroscopicity can be obtained by drying a hydrous crystal of Compound (1) under a specific reduced pressure with heating. The present invention was achieved on the basis of this finding.

The present invention thus provides an anhydrous crystal of a compound represented by the general formula: $R^2$—$CH_2CONH$—$R^1$ wherein $R^1$ represents a substituted or non-substituted pyridyl group or substituted or non-substituted phenyl group; and $R^2$ represents a substituted or non-substituted 2-oxo-1-pyrrolidinyl group, characterized in that said crystal is substantially free from hygroscopicity. According to a preferred embodiment of the present invention, there is provided the aforementioned crystal which gains 1% or less weight increase when stored at a temperature of 25° C. for 30 day under a relative humidity of 83%.

According to another aspect of the present invention, there is provided a method for preparing the aforementioned crystal which comprises the step of drying a crystal of the compound represented by the above formula at a temperature of 80° C. or above under reduced pressure. According to preferred embodiments of this invention, there are provided the aforementioned process wherein a hydrous crystal of the above compound is dried; the aforementioned process wherein water content of the hydrous crystal is 20% or less; the aforementioned process wherein the drying step is carried out at a temperature between the range of from 110 to 120° C.; and the aforementioned process wherein reduced pressure of 50 mmHg or lower is applied.

BEST MODE FOR CARRYING OUT THE INVENTION

Figure 1:
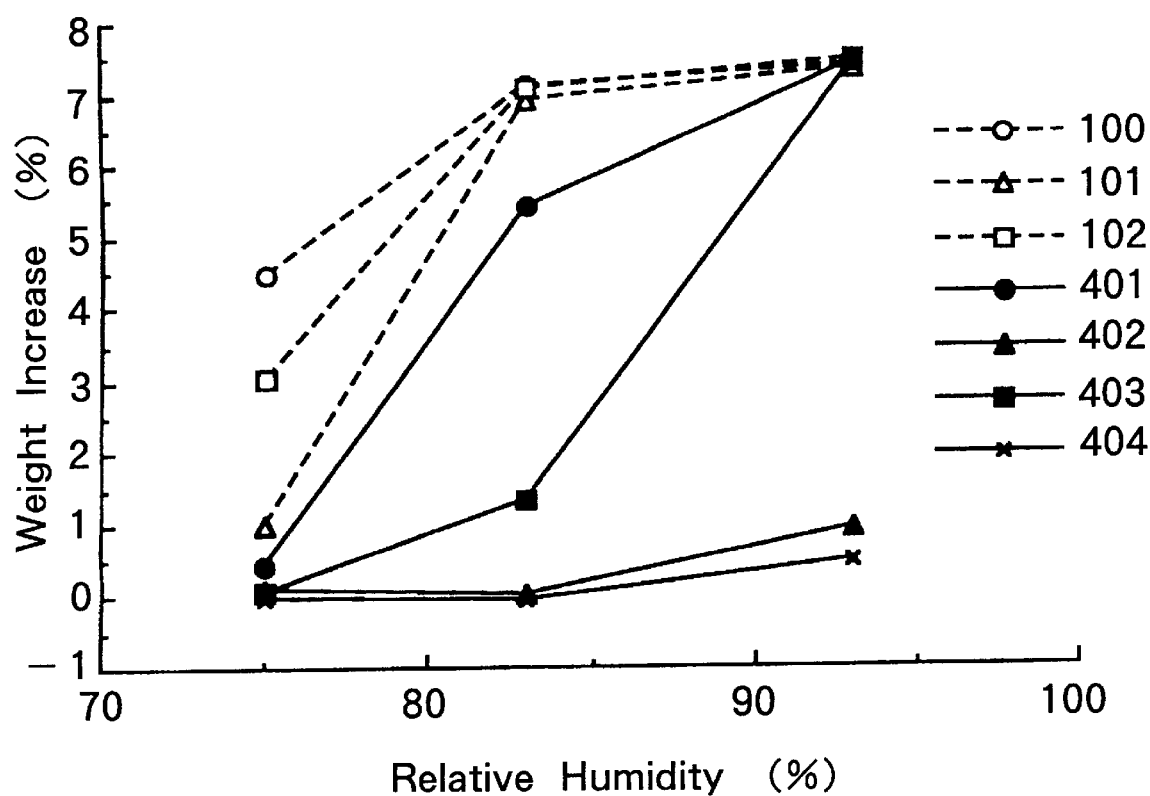
FIG. 1 shows weight increases of anhydrous crystals of Compound (1) when stored under a relative humidity of 75%, 83%, or 93% for 30 days. In the figure, the lot numbers 402 and 404 represent the anhydrous crystals of the present invention.

In the above general formula, the substituents of the substituted pyridyl group or the substituted phenyl group, or those of the 2-oxo-1-pyrrolidinyl group are not particularly limited. Examples of the substituents include a $C_{1-6}$ alkyl group, a $C_{1-6}$ alkoxy group, a halogen atom, a halogenated $C_{1-6}$ alkyl group, cyano group, nitro group, a $C_{1-6}$ alkoxy-substituted carbonyl group, a $C_{1-6}$ alkyl-substituted carbonyl group, hydroxyl group, carboxyl group, substituted or non-substituted amino group or the like. Examples of the substituted amino group include amino groups substituted with one or two $C_{1-6}$ alkyl groups (where two substituents exist, they may be the same or different from each other). The alkyl group and the alkoxy group may be straight- or branched-chain groups. The pyridyl group and the phenyl group may have one or more substituents as mentioned above on their rings.

Among the compounds represented by the above general formula, the above-mentioned Compound (1) [N-(2,6-dimethylphenyl)-2-(2-oxo-1-pyrrolidinyl) acetamide] is preferred. However, compounds that constitute the crystals of the present invention are not limited to this particular compound.

The crystals of the present invention are anhydrous crystals of the compounds embraced by the above general formula and characterized in that they are substantially free from hygroscopic property. The inventors of the present invention have revealed that at least three kinds of anhydrous crystals of a compound of the above general formula exist. More specifically, as anhydrous crystals of Compound (1) which is a typical compound among those of the above general formula, there exist (a) a crystal substantially free from hygroscopicity when stored under a relative humidity of 83% for 30 days; (b) a crystal which exhibits a weight increase but not reaches to hygroscopic equilibrium when stored under a relative humidity of 83% for 30 days; and (c)

a crystal which exhibit a weight increase and reaches to hygroscopic equilibrium to form a monohydrate when stored under a relative humidity of 83% for 30 days. The crystal of the present invention is characterized to have the same property as those defined by the above (a).

The characteristics of the crystal of the present invention are further explained more specifically by referring to FIG. 1. FIG. 1 depicts the weight increases of anhydrous crystals of Compound (1) when stored under a relative humidity of 75%, 83%, or 93% for 30 days. Under the relative humidity of 83%, the crystals of the lot numbers 402 and 404 exhibited no weight increase (crystals of the present invention: crystals of the above (a)). The crystals of the lot numbers 101, 401, and 403 exhibited apparent weight increases, whilst they did not reach to complete hygroscopic equilibrium under the relative humidity of 83% (crystals of the above (b)). The crystals of the lot numbers 100 and 102 exhibited apparent weight increase and reached to complete hygroscopic equilibrium under the relative humidity of 83%(crystals of above (c)).

The method of the present invention is characterized in that a starting material is kept under reduced pressure and dried at a temperature of 80° C. or above to obtain the anhydrous crystal according to the above (a). As the starting materials for the method of the present invention, any hydrous crystals of a compound embraced by the above general formula (hydrate crystals containing any numbers of water of crystallization), or anhydrous crystals having the same moisture absorbing properties as those of the above (b) or (c) can be used. Among them, hydrous crystals may preferably be used. Where anhydrous crystals having the same hygroscopic properties as those of (b) or (c), which are characterized by their high moisture absorption rates, are used as starting compounds, they can be converted into the anhydrous crystals of the present invention by first converting them into hydrous crystals by recrystallization, and then subjecting the result to the drying step, or alternatively, by subjecting them directly to the treatment according to the method of the present invention.

When crystals such as hydrous crystals or the anhydrous crystals are used as the starting compounds, average particle size, particle size distribution, or apparent specific volume and the like of the crystals are not particularly limited. For example, those having an average particle size of 31 to 51 μm; a particle size distribution of 106 to 500 μm which constitutes 75 to 90% of the whole particles; and an apparent specific volume of 1.41–1.48 ml/g may preferably be used. Conditions for crystallization, (e.g., cooling rate, agitation rate, and pH during crystallization) to prepare these crystals used as starting compounds are also not particularly limited. Where hydrous crystals are used, it is preferred to use those having an initial water content as low as possible. For example, those having a water content of 20% or less, particularly 15% or less are preferred. It is not preferable to use crystals having initial water content of above 20%, because anhydrous crystals with high hygroscopic rate may sometimes be obtained.

Drying step can be carried out at a temperature of 80° C. or above, preferably 100° C. or above, most preferably between the range of from 110 to 120° C. In general, the above compounds will not decompose or color when heated, for example, at 100° C. for about 24 hours. However, drying at an unnecessarily high temperature is not preferable because such step may be disadvantageous from an economical viewpoint and may cause decomposition or melt of the compounds. A drying temperature of 60° C. or less is not preferred because such step may sometimes give anhydrous crystals with high hygroscopic rate. The above-mentioned drying temperature means a temperature of the object, per se, to be dried. Therefore, in general, it is necessary to carry out the drying step by adjusting a temperature of a drying apparatus at several to several tens of degrees (°C.) higher to achieve a desired internal temperature of an object.

The reduced pressure may be 200 mmHg or lower, preferably 100 mmHg or lower, more preferably 50 mmHg or lower, and most preferably between the range of from 35 to 45 mmHg. Generally, the anhydrous crystal of the present invention can be efficiently obtained by carrying out the drying step under a higher level of vacuum. However, a suitable reduced pressure should be chosen from economical and operative viewpoints and other. A drying step under a poor level of vacuum such as 300 to 400 mmHg is not preferred, because such step may sometimes give anhydrous crystals with high hygroscopic rate. Drying procedures are not particularly limited, and those commonly used by skilled artisans, for example, a fluidizing drying method using an evaporator, a compartment tray drying method, a vibro-fluidizing drying method or the like may be applied. Time for drying is generally 1 to 24 hours, preferably 5 to 15 hours, more preferably 10 to 12 hours, and most preferably about 9 hours.

The crystals of the present invention obtained as described above may sometimes have so-called adhered water on the surfaces thereof. It will be readily understood by those skilled in the art that such adhered water is not derived from water molecules that form the crystal lattice. Water content derived from such adhered water is generally 1% or less, preferably 0.2% or less. The anhydrous crystals of the present invention do not substantially exhibit weight increase due to moisture absorption when stored, for example, under the relative humidity of 83% at the temperature of 25° C. for 30 days. Therefore, any anhydrous crystals that exhibit weight increase of 1.0% or less when measured under conditions substantially the same as those mentioned above fall within the scope of the present invention. Preferable crystals according to the present invention exhibit weight increase of 0.5% or less, more preferably 0.1% or less, when measured under the conditions mentioned above.

Although it is not intended to be bound by any specific theory, a prospective reason of the existence of plural anhydrous crystals of the aforementioned compound having distinguishable hygroscopic rates is that differences in surface structures, i.e., unevenness of the surfaces and the diameter and numbers of micropores or other, may arise depending on the drying condition. For example, where the drying step is carried out at a low temperature, micropores are formed by the turbulence of crystal surfaces due to dehydration from the surfaces and the diffusion and migration of water molecules from inside portions, which results in the formation of light weight crystals with turbulent surfaces that exhibit a high hygroscopic rate. On the other hand, where drying is carried out at a high temperature, destruction or recrystallization with partial fusion of crystals may occur due to rapid dehydration, which results in the formation of heavy weight crystals having smooth surfaces to give crystals with a low hygroscopic rate. However, it should be understood that the scope of the present invention is not limited from the viewpoint of the surface structures of crystals or the like as mentioned above.

EXAMPLES

The present invention will be explained more specifically by referring to examples. However, the present invention is not limited to these examples.

Example 1

Ten grams of the hydrate of Compound (1) [N-(2,6-dimethylphenyl)-2-(2-oxo-1-pyrrolidinyl)acetamide] (water content: 13.2%, Karl Fischer's method) was dried under a pressure of 35–45 mmHg at a drying temperature of 110–120° C. for 9 hours to give 8.5 g of the anhydrous crystals of the present invention. For a comparison, the hydrate was dried at a lower temperature of 60–70° C. in a similar manner to give anhydrous crystals with a high hygroscopic rate (anhydrous crystals of the above (c)).

The anhydrous crystals were sifted by using a 60 mesh sieve. One gram sample of the crystals passed through the sieve was kept under a constant humid condition in a desiccator (20° C., relative humidity of 85% over a saturated KCl solution) to evaluate hygroscopic rates of the crystals. The ratios of weight increase observed in this experiment are shown in Table 1 (the ratios of weight increase were calculated on the basis of crystals having the highest hygroscopic rate, and "1" represents that crystals have the highest hygroscopic rate).

TABLE 1

| Period of Time | 1 week | 2 weeks |
| --- | --- | --- |
| Ratio of weight increase | 0.020 | 0.185 |

Example 2

Twenty grams of the above hydrate of Compound (1) was dried under the pressure of 40 mmHg at a drying temperature of 110–120° C. for 9 hours to obtain 17.0 g of the anhydrous crystals of the present invention. The anhydrous crystals were sifted by using a 60 mesh sieve. One gram sample of the crystals passed through the sieve was kept under a constant humid condition in a desiccator (20° C., relative humidity of 85% over a saturated KCl solution) to evaluate hygroscopic rates of the crystals. The ratios of weight increase are shown in Table 2.

TABLE 2

| Period of time | 1 week | 2 weeks |
| --- | --- | --- |
| Ratio of weight increase | 0.173 | 0.460 |

Example 3

The anhydrous crystals of Compound (1), which was prepared by the method of Example 1 and corresponded to the above (c), were sifted by using a 60 mesh sieve. Twelve-gram sample of the crystals passed through the sieve was dried at a drying temperature of 110–120° C. and 1 g samples of the crystals were continually collected. These samples were kept under a constant humid condition in a desiccator (20° C., relative humidity of 85% over a saturated KCl solution) to evaluate hygroscopic rates of the crystals. As apparent from the results set out below, the anhydrous crystals with high hygroscopic rate were converted into anhydrous crystals of the present invention having the low hygroscopic rate by the prolonged heating treatment.

TABLE 3

| Time (h) | 0 | 8 | 16 | 24 | 32 |
| --- | --- | --- | --- | --- | --- |
| Ratio of weight increase | 1.00 | 0.13 | 0.15 | 0.09 | 0.08 |

Industrial Applicability

The anhydrous crystals of the present invention exhibit substantially no moisture absorption when stored for a long period of time under a highly humid condition. Therefore, when they are used for the manufactures of medicaments that comprises a compound of the above general formula as an active ingredient, products having a constant content of the active ingredient can be provided. The method of the present invention is useful because it enables the manufacture of the above anhydrous crystals in a large scale with excellent reproducibility.

What is claimed is:

1. An anhydrous crystal of a compound represented by the following formula:

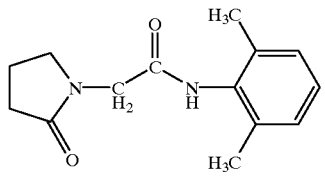

wherein said crystal is substantially free from hygroscopicity, and which exhibits a weight increase of 1% or less when stored under a relative humidity of 83% at a temperature of 25° C. for 30 days.

2. A method for preparing an anhydrous crystal of a compound represented by the following formula:

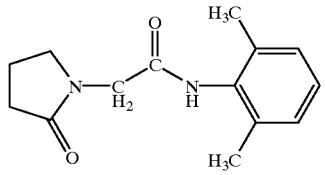

which is substantially free from hygroscopicity, which comprises drying a crystal of the compound at a temperature of at least 80° C. under reduced pressure.

3. The method according to claim 2, wherein the anhydrous crystal exhibits a weight increase of 1% or less when stored under a relative humidity of 83% at a temperature of 25° C. for 30 days.

4. The method according to claim 3, wherein the crystal of the compound comprises a hydrous crystal of the compound.

5. The method according to claim 4, wherein water content of the hydrous crystal is 20% or less.

6. The method according to claim 2, wherein the crystal of the compound comprises a hydrous crystal of the compound.

7. The method according to claim 6, wherein water content of the hydrous crystal is 20% or less.

8. The method according to claim 2, wherein the drying is carried out at a temperature between 110 to 120° C.

9. The method according to claim 3, wherein the drying is carried out at a temperature between 110 to 120° C.

10. The method according to claim 4, wherein the drying is carried out at a temperature between 110 to 120° C.

11. The method according to claim 6, wherein the drying is carried out at a temperature between 110 to 120° C.

12. The method according to any one of claims 2, wherein the reduced pressure comprises a reduced pressure of 50 mm Hg or lower.

13. The method according to any one of claims 3, wherein the reduced pressure comprises a reduced pressure of 50 mm Hg or lower.

14. The method according to any one of claims 10, wherein the reduced pressure comprises a reduced pressure of 50 mm Hg or lower.

15. An anhydrous crystal of a compound represented by the following formula:

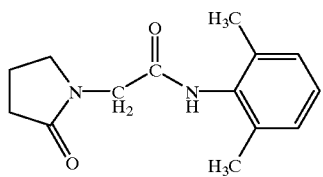

which is substantially free from hygroscopicity, which exhibits a weight increase of 1% or less when stored under relative humidity of 83% at a temperature of 25° C. for 30 days, and which is obtained by a process comprising drying a crystal of the compound at a temperature of at least 80° C. under reduced pressure.

16. A pharmaceutical composition comprising as an active ingredient the anhydrous crystal according to claim 1.

17. A pharmaceutical composition comprising as an active ingredient the anhydrous crystal according to claim 16.

* * * * *

UNITED STATES PATENT AND TRADEMARK OFFICE
CERTIFICATE OF CORRECTION

PATENT NO. : 6,169,108 B1  
DATED : January 2, 2001  
INVENTOR(S) : Y. Sato et al.

Page 1 of 1

It is certified that error appears in the above-identified patent and that said Letters Patent is hereby corrected as shown below:

<u>Title page,</u>
Item [56] References Cited, FOREIGN PATENT DOCUMENTS, the following reference was omitted and should be included:
-- 56-2960     1/1981         (JP) --

<u>Column 8,</u>
Line 19, "claim 16" should be -- claim 15 --.

Signed and Sealed this

Fifth Day of March, 2002

*Attest:*

*Attesting Officer*

JAMES E. ROGAN  
*Director of the United States Patent and Trademark Office*